United States Patent [19]

Seng et al.

[11] Patent Number: 4,549,897

[45] Date of Patent: Oct. 29, 1985

[54] PROTEIN DEGRADED PRE-VULCANIZED NATURAL RUBBER COATED SLOW RELEASE FERTILIZERS

[75] Inventors: Yeoh C. Seng; Chen S. Fong, both of Kuala Lumpur, Malaysia

[73] Assignee: Petroliam Nasional Berhad, Kuala Lumpur, Malaysia

[21] Appl. No.: 408,774

[22] Filed: Aug. 17, 1982

[30] Foreign Application Priority Data

Aug. 20, 1981 [GB] United Kingdom ............... 8125458

[51] Int. Cl.$^4$ ........................................... A01N 25/26
[52] U.S. Cl. ............................................ 71/3; 71/27;
71/64.11; 71/64.13; 71/64.07; 71/903
[58] Field of Search ............ 435/267; 71/64.11, 64.13,
71/27, 11, 903, 904, 64.07, 64.02, 28, 3

[56] References Cited

U.S. PATENT DOCUMENTS

| 2,511,722 | 6/1950 | Lepetit | 435/267 |
| 3,639,259 | 2/1972 | Scarpelli | 71/64.11 X |
| 44-28457 | 1/1969 | Mueller | 71/64.11 |

FOREIGN PATENT DOCUMENTS

| 1047272 | 1/1979 | Canada | 71/64.11 |
| 4428457 | 1/1965 | Japan | 71/27 |

*Primary Examiner*—Ferris H. Lander
*Attorney, Agent, or Firm*—Wenderoth, Lind & Ponack

[57] ABSTRACT

An agricultural material composition comprises particles of an agricultural material, e.g. a fertilizer, coated with a layer of protein degraded pre-vulcanized natural rubber to provide slow-release properties. The particles preferably have a diameter of from 0.5 to 12 mm, and the thickness of the rubber layer is preferably from 10 to 250 microns.

9 Claims, No Drawings

PROTEIN DEGRADED PRE-VULCANIZED NATURAL RUBBER COATED SLOW RELEASE FERTILIZERS

This invention relates to the use of natural rubber (NR) in the manufacture of coated agricultural materials. In particular it relates to the manufacture of slow release fertilizers by coating fertilizer materials with a coating of NR derived from a modified NR latex.

It is well known that many conventional fertilisers are highly soluble in water, and when applied to soils, particularly sandy soils, a high proportion of them will be rapidly leached away from the rhizospheres (root zones) of plants resulting in depletion of the effective nutrient supply to the plants. This leaching problem is particularly serious in tropical countries where rainfall intensities are high. A reasonably constant supply of nutrients in the rhizosphere throughout the growing season is of great importance. To overcome these problems, the use of various types of slow-release fertilisers has been suggested. Such fertilisers release nutrients slowly when applied to the soild and in doing so provide a more nearly continuous supply of nutrients, hence reducing leaching losses.

Our experimental work has shown that fertilizers coated with unmodified NR are rapidly leached despite the coating of rubber. This appears to be a result of the relatively highly permeable and hydrophilic nature of the rubber deposited on the fertilizer from NR latex. Further, if the latex is not vulcanized then there is a strong tendency for the coated fertilizer particles to aggregate to an undesirable extent, because the rubber film is relatively soft and tacky. The use of pre-vulcanized latex permits avoidance of the problem of aggregation but the rubber film is still sufficiently hydrophilic and permeable that it is not of practical value in the manufacture of slow release fertilizers.

The use of synthetic polymers has been proposed but many of these give virtually impermeable films around the particles of fertilizer and the distribution of fertilizer to the rhizosphere is impractically slow. Further, many synthetic polymers are normally not fully biodegradable and can give rise to residues which may have a deleterious effect on nearby plants.

The present invention is based on the discovery that coating fertilizers with a modified natural rubber latex in which the rubber is prevulcanized and the proteins are at least partly degraded gives a product which provides a particularly useful balance of properties to suit it for use as a slow-release fertilizer.

Accordingly, the present invention provides a slow release fertilizer which comprises a fertilizer coated with a layer of protein degraded pre-vulcanized natural rubber. The invention includes a method of making a slow release fertilizer which comprises contacting particles of a fertilizer with a protein degraded pre-vulcanized natural rubber latex and coagulating and drying the rubber on the particles of the fertilizer thereby coating the particles with a film of protein degraded pre-vulcanized natural rubber. The particular method by which the protein degraded prevulcanized rubber (PD-PV NR) is coated onto the particles of fertilizer is not critical to the overall method of the invention. Thus, techniques such as pan coating, rotary drum coating and similar methods can be used. However, we have found that a fluidized bed technique is particularly appropriate and, accordingly, forms a further aspect of the invention. In this further aspect the invention provides a method of making a slow release fertilizer which comprises providing a fluidized bed of particulate fertilizer and introducing into the bed protein degraded prevulcanized natural rubber latex in droplet form whereby to form a coating of dried coagulated protein degraded prevulcanized natural rubber over the fertilizer particles. This method can be carried out in a batch process by placing the fertilizer, preferably in granular form, in a vessel having a perforated base and pumping heated air through the base to fluidize the fertilizer granules. The PD-PV NRL can be introduced into the fluidized bed by spraying it e.g. using a compressed air sprayer into the bed. The nozzles of the sprayer are conveniently positioned at the bottom of or within the fluidized bed. The latex spray forms a coating which coalesces into a coherent film on the surface of the fertilizer granules and rapidly coagulates and dries in the stream of hot air used for fluidizing. The rapid drying of the rubber film avoids problems which might otherwise occur by the granules sticking together thus forming undesirably large aggregates or tearing the rubber film off the granules. After the desired amount of latex has been sprayed onto the granules it is desirable to maintain them in a fluidized state to ensure thorough drying of the latex to give a non-tacky tough film of PD-PV NR. Granules coated in this way can readily be stored for subsequent use in bags or drums.

The natural rubber used in this invention to make slow release fertilizers is protein degraded pre-vulcanized natural rubber latex (PD-PV NRL). To the best of our knowledge this form of natural rubber latex is novel. Prevulcanized natural rubber latex (PV NRL) has long been known and used in the manufacture of latex products e.g. rubber gloves. Also, techniques for making deproteinized natural rubber are known e.g. as described in our earlier British Patent Specification No. 1366934. In this prior Specification, the rubber is deproteinized by treating the latex with a proteolytic enzyme to hydrolyse the protein fraction of the latex, diluting the latex typically to about 3% dry rubber content (drc) and then coagulating the latex with acid to produce solid rubber. The reason for the treatment is to achieve an improvement in the properties and behaviour of the rubber produced in the raw state and/or after vulcanization of the solid rubber. These improved properties are not particularly relevant to the manufacture of rubber latex goods and, in any event, the separation of the rubber from the protein hydrolysis products usually involves acid coagulation of the latex.

In the present invention it is not necessary to separate the rubber from the hydrolysis products, indeed, we have found that it is beneficial to the slow-release fertilizer product not to remove the hydrolysis products from the latex. The hydrolysis of the proteins is most conveniently carried out by treating the latex with a proteolytic enzyme for example by the method described in British Patent Specification No. 1366934.

Although it is not necessary to remove the protein degradation products from the latex we have found that slow release fertilizers can be made using fully deproteinised prevulcanized natural rubber (DP-PV NR) and, accordingly this is included within the term "protein degraded prevulcanized natural rubber". Deproteinized natural rubber latex (DP NRL) can be made by successive dilution and concentration e.g. by centrifuging, of latex in which the proteins have been degraded e.g. by enzymatic hydrolysis. As those skilled in the art will appreciate the dilution/concentration method can be used to reduce the proportion of protein degradation products in rubber coagulated from the latex to any desired extent and thus it provides a technique for choosing a desired level of protein degradation products in the rubber. The use of fully deproteinized pre-vulcanized rubber latex (DP-PV NRL) tends to give fertilizers having extended slow release characteristics. This can be used to advantage by blending fertilizers coated with DP-PV NR with fertilizers coated with PD-PV NR to obtain a combination of properties. However, the use of DP-PV NR involves significant additional processing costs usually with only small technical advantages possible and, accordingly, it is not especially preferred.

The latex may be pre-vulcanized by known techniques for example by heating the latex typically at about 70° C. for 1 to 2 hours with a suitable vulcanizing ingredient such as a mixture of sulphur, zinc diethyl dithiocarbamate and zinc oxide. It is usual to stabilize the latex against coagulation during pre-vulcanization by adding to it an involatile alkali e.g. KOH or carboxylic acid soaps in suitable amounts.

We have found that PD-PV NRL suitable for manufacture of slow-release fertilizers can be made either by first treating the latex with a proteolytic enzyme and then prevulcanizing or by first pre-vulcanizing the latex followed by treatment with a proteolytic enzyme. The form of latex used as the starting material is not critical and we have obtained satisfactory results using field latex, concentrated e.g. centrifuge concentrated, latex and skim latex.

The present invention relates to coating general types of fertilizer but is particularly directed to coating fertilizers which are water soluble or readily water dispersible because such fertilizers are especially susceptible to being rapidly leached from the rhizosphere. These fertilizers include inorganic salts such as potassium and ammonium salts of sulphuric, nitric and phosphoric acids. It is usual practice to assay such fertilizers in terms of their potassium (K) phosphorus (P) and nitrogen (N) contents. Organic fertilizers such as urea can also be used. Additionally, with ammonia-containing fertilizers such as urea and inorganic ammonium salts, coating the fertilizers with PD-PV NR reduces the loss of nitrogen to the atmosphere by volatilization of ammonia. This is particularly significant in tropical environments where ammonia volatilization especially from urea is a major disadvantage of such fertilizers. The fertilizer can be a single compound (a "straight" fertilizer) or a mixture of compounds (a "compound" fertilizer) as may be desired to suit particular circumstances. These fertilizers can be used alone or in combination with other materials having desired activity in the rhizosphere e.g. plant growth regulants, hormones, pesticides, weedkillers and agents active against undesired soil microorganisms. Further, we we have found that coating granules including seed and fertilizers according to the invention is particularly beneficial.

In this connection we have found that the invention can be of applicability to the coating of particulate agricultural materials generally and is not limited to fertilizers liable to leaching. Accordingly, the present invention in a further aspect includes a particulate agricultural material coated with a film of protein degraded prevulcanized natural rubber and a method of making a coated agricultural material which comprises contacting the particulate agricultural material with a protein degraded pre-vulcanized natural rubber latex and coagulating and drying the rubber on the particles of the agricultural material thereby coating the particles with a film of protein degraded pre-vulcanized natural rubber. The agricultural materials to which this apsect of the invention relates include, in addition to fertilizers, plant growth regulants, hormones, pesticides, weed killers, seeds and agents active against undesired, or active to encourage desired soil microorganisms. Where these materials are not particulate they may be adsorbed on or absorbed in a suitably particulate carrier which may be another agricultural method or an inactive or inert particulate carrier.

The film of rubber coating the particulate fertilizer or agricultural material may be modified by inclusion therein of materials such as preservatives, stabilizers, antioxidants, surfactants, inert fillers, viscosity modifiers, compatibility agents, co-solvents and humectants. Usually such materials, if used, will be added to the rubber latex prior to coagulation.

The particulate slow release fertilizer according to the invention will typically be made to have an average particle size of from 0.5 to 12 mm. The precise figure in any particular case will be selected to suit the intended use of the fertilizer. Generally, other coated agricultural materials will be made in a similar particle size range.

The thickness of the film of PD-PV NR around the particles of fertilizer is an important factor in determining the release characteristics of the coated fertilizer. However, direct measurement of the film thickness is difficult. Accordingly, it is generally more convenient to refer to the weight percent of rubber, based on the fertilizer. Whilst the film thickness is a function of the weight percent rubber it is also a function of the particle size. Thus, assuming that the particles are spherical, that their specific gravity is 1.33 and that the specific gravity of the rubber film is 0.92 a coating of 10% by weight of rubber on particles 4 mm in diameter gives an average (calculated) film thickness of about 90 $\mu$m. To achieve this thickness on particles 2 mm in diameter would require about 21% by weight of rubber and on 0.5 mm particles about 108% by weight of rubber in the coating. Generally, the thickness of the film will be in the range 10 to 250 $\mu$m. Correspondingly the amount of rubber coated onto the particles will generally be from 1 to 25% preferably 5 to 5%, by weight on the weight of the fertilizer. It will be recognized that within this range the higher precentages will more usually be applicable to particles of smaller size within the size range given above and vice versa. In any particular case the amount of rubber in the coating will, be selected to give the desired slow release characteristic as the thicker the coating film the slower the release of fertilizer.

If it is desired to slow down the leaching of fertilizer even further than is obtained using PD-PV NR then this may be achieved by including a minor proportion of a synthetic polymer in the coating of the fertilizer. A proportion of up to 45% of the coating may be made of synthetic polymer for this purpose. The synthetic polymer is preferably included in the rubber latex prior to coagulation typically as a latex or emulsion. The amount of synthetic polymer latex or emulsion used depends on the desired proportion of synthetic polymer in the rubber film, the dry rubber content of the PD-PV NRL and the polymer content of the synthetic polymer or latex.

We do not fully understand why the use of PD-PV NRL in coating fertilizers is as successful as it is, but it seems that the following factors contribute to the result. Pre-vulcanization of the latex reduces the water and fertilizer permeability of the rubber film to a moderate extent but not sufficiently to provide a satisfactory slow-release product. We believe that films made from pre-vulcanized (but not protein degraded) latex include significant proportions of proteinaceous material, largely made up of intact or only slightly degraded proteins in the latex. The protein molecules are lrage and are hydrophilic and, in contact with water, become hydrated and from large hydrophilic pathways through the rubber film thus permitting relatively rapid leaching. The relatively high concentrations within the coated fertilizer particles provides a susbstantial driving force which enhances the effectiveness of any hydrophilic pathways. In rubber films formed from PD-PV NRL, degradation products of the proteins in the original latex will normally be present. Generally, these degradation products are much smaller in size than the proteins in non-protein-degraded rubber, and accordingly form smaller hydrophilic channels in the rubber film. Thus, the presence of the degradation products imparts a degree of hydrophilicity and permeability to the rubber film which can, to some extent, be controlled by the thickness of the rubber film and the choice of additives. The inclusion of synthetic polymer is, as described above, a further way of modifying the hydrophilicity and permeability of the film.

The following Examples illustrate the invention. Example 1 describes techniques for carrying out the pre-vulcanization and protein degradation steps to make a PD-PV NRL suitable for use in the invention and describes some of the properties of such latex. Example 2 describes the manufacture and Examples 3 to 5 the properties of slow release fertilizers according to the invention.

EXAMPLE 1

Protein Degradation

To proteins in the NR latex were degraded by treating NR latex with a proteolytic enzyme as described in British Patent Specification No. 1366934. The degraded protein fractions were not removed from the latex. The degree of protein-breakdown was assessed by analysing for the nitrogen content of the dry rubber obtained by coagulating the latex, with acid.

Vulcanisation

This was effected by heating the NR latex with vulcanising ingredients at about 70° C. for 1–2 hours. The vulcanising ingredients used were a mixture of sulphur, zinc diethyl dithiocarbamate and zinc oxide although other vulcanizing systems could be used. The latex can be stabilised by the incorporation of stabilising agents as potassium hydroxide, or carboxylic acid soaps where necessary.

The PD-PV NRL obtained by the protein degradation and pre-vulcanization steps above and conventional prevulcanized natural rubber latex (PV NRL)(for comparison) were diluted to 3% solids content and coagulated by addition of acid. The nitrogen content in the coagulated rubber was determined analytically and the corresponding protein content present was estimated by multiplying the nitrogen content by a factor of 6.25. The results are given in Table 1. For comparison the protein content of the latex either PD-PV NRL or PV NRL, obtained by nitrogen analysis of the total solids film from drying the latex at 70° C. in an oven, was about 1.9%. Table 1 shows that protein-degraded prevulcanised samples, (2) and (3) have markedly lower protein content than prevulcanised NR latex (1). It also shows that the protein can be effectively degraded either before or after vulcanisation of the latex.

TABLE 1

| Sample No | NR latex sample | Protein content (% by weight on dry rubber) |
|---|---|---|
| (1) | Prevulcanised (comparison) | 0.94 |
| (2) | Protein-degraded, followed by prevulcanisation | 0.30 |
| (3) | Prevulcanised, followed by protein-degradation | 0.20 |

EXAMPLE 2

Granules of a commercially available inorganic fertilizer containing potassium, nitrogen and phosphorus, having an average diameter of about 3 to 4 mm were fluidized in a bed using a stream of hot air. PD-PV NRL was sprayed into the bed from the bottom at a rate to uniformly coat the granules. The coating weight was 14.2% by weight of rubber. The Example was repeated using PV NRL to a coating weight 14.6% by weight of rubber to provide a comparative sample. The Example was further repeated using granules having an average diameter of about 2 to 3 mm of urea wth both PD-PV NRL and PV NRL both to a coating weight of 13%.

EXAMPLE 3

Leaching studies

The experiments on the leaching of the fertilizers coated with PD-PV NR and PV NR(for comparison) formulations were conducted using a sand-filled glass tube of 5 cm in diameter and 40 cm in height.

Granules of the coated inorganic fertilizer produced in Example 2 were placed on top of the sand column and 25 ml of distilled water was applied alternate-daily to the tube.

Leaching collection was made weekly by providing a suction pressure of 100 cm water to the outlet. The leachates were analysed for nitrogen, phosphorus and potassium.

TABLE 2

| Fertiliser samples | Elements | Percentage Cumulative leaching loss | | | | |
| | | 2 weeks | 4 weeks | 6 weeks | 8 weeks | 10 weeks |
|---|---|---|---|---|---|---|
| Coated with PV NR 14.6% by wt. rubber based on fertiliser | N | 52.5 | 80.9 | 92.3 | 97.6 | 100 |
| | P | 1.4 | 10.2 | 16.3 | 19.8 | 21.7 |
| | K | 37.3 | 57.8 | 68.2 | 75.2 | 80.6 |
| Coated with PD-PV NR 14.2% by wt. rubber based on fertiliser | N | 6.0 | 38.6 | 61.6 | 74.0 | 80.5 |
| | P | 0 | 2.4 | 9.5 | 14.5 | 18.2 |
| | K | 4.1 | 26.7 | 44.9 | 56.5 | 67.5 |

The comparative leaching results for nitrogen, phosphorusand potassium as given in Table 2 show clearly that PD-PV NR coating is far superior to PV NR in reducing the leaching rates of these elements.

EXAMPLE 4

Dislodgement studies

The experiments on the rate of dislodgement of the fertilizer elements from the coated granules as affected by rain and sunlight were carried out in a glasshouse. These involved spreading a fixed amount of granules of coated inorganic fertiliser produced in Example 2 over a series of potted soils, exposing such granules to sunlight and watering them daily with a fixed amount of rain water to simulate the Malaysian rainfall conditions. These fertilizer granules were removed at fortnightly intervals and the quantity of fertiliser elements remaining in them was determined analytically. The results are given in Table 3.

TABLE 3

| Fertiliser samples | Elements | Percentage of fertiliser elements left in coated granules | | | | |
|---|---|---|---|---|---|---|
| | | 2 weeks | 4 weeks | 6 weeks | 8 weeks | 10 weeks |
| Coated with PV NR 14.6% by wt. rubber based on fertiliser | N | 27.1 | 14.0 | 12.7 | 7.7 | 5.2 |
| | P | 74.4 | 67.2 | 66.7 | 59.0 | 54.6 |
| | K | 42.8 | 28.0 | 24.4 | 18.0 | 11.7 |
| Coated with PD-PV NR 14.2% by wt. rubber based on fertiliser | N | 70.2 | 52.1 | 32.2 | 18.4 | 16.1 |
| | P | 90.6 | 78.1 | 72.8 | 67.7 | 63.3 |
| | K | 76.4 | 56.1 | 37.7 | 34.6 | 28.5 |

The comparative data on retention of nitrogen, phosphorus and potassium in the coated granules show clearly that PD-PV NR coating is far more effective than PV NR in slowing down the dislodging rates of these elements.

EXAMPLE 5

Diffusion studies

The rate of diffusion of nutrients from PD-PV NR coated urea was compared with that of PV NR coated urea both produced in Example 2. This experiment was conducted by immersing 5 g of each sample in 500 ml distilled water in a flask. 2 ml sample solutions were removed from each flask at intervals of every 24 hours. In each case, the flask was gently inverted 10 times before the removal. The nitrogen in the aqueous solution was determined and the results are given in Table 4.

TABLE 4

| Rubber Latex Used | Amount of Rubber in Coating | Percentage of N diffused from coated urea into aqueous solution | | | | | |
|---|---|---|---|---|---|---|---|
| | | 1 day | 2 days | 3 days | 4 days | 5 days | 7 days |
| PV NRL | 13.0% | 99.0 | 100 | — | — | — | — |
| PD-PV NRL | 13.0% | 32.9 | 50.0 | 66.6 | 81.1 | 88.8 | 96.7 |

The results show conclusively that PD-PV NR formulation is much more effective than that of PV NR as a coating material for controlling the diffusion of urea into a surrounding aqueous medium.

We claim:

1. The slow release fertilizer composition which comprises particles of a fertilizer coated with a layer of protein degraded pre-vulcanized natural rubber.

2. A composition as claimed in claim 1 wherein the fertilizer is a potassium or ammonium salt of sulphuric, nitric or phosphoric acids or urea or a mixture thereof.

3. An agricultural material composition which comprises particles of an agricultural material selected from the group consisting of plant growth regulants, hormones, pesticides, weed killers, seeds and agents active against undesired, or active to encourage desired soil microorganisms coated with a layer of protein degraded pre-vulcanized natural rubber.

4. The composition as claimed in any one of claims 1 to 3 wherein the particles have a diameter of from 0.5 to 12 mm.

5. The composition as claimed in any one of claims 1 to 3 wherein the thickness of the layer of rubber is from 10 to 250 μm.

6. The composition as claimed in any one of claims 1 to 3 wherein the amount of rubber in the coating is from 1 to 25% by weight on the weight of the particles.

7. A method of making a slow release fertilizer composition which comprises contacting particles of a fertilizer with a protein degraded pre-vulcanized natural rubber latex and coagulating and drying the rubber on the particles of the fertilizer thereby coating the particles with a film of protein degraded pre-vulcanized natural rubber.

8. The method of making a coated particulate agricultural material composition which comprises contacting particles of an agricultural material selected from the group consisting of plant growth regulants, hormones, pesticides, weed killers, seeds and agents active against undesired, or active to encourage desired soil microorganisms with a protien degraded prevulcanized natural rubber latex and coagulating and drying the rubber on the particles of the agricultural material thereby coating the particles with a film of protein degraded pre-vulcanized natural rubber.

9. The method as claimed in either claim 7 or claim 8 comprising providing a fluidized bed of the particles and introducing into the bed protein degraded natural rubber latex in droplet form whereby to form a coating of protein degraded natural rubber over the particles.

* * * * *